United States Patent
DeLuca et al.

(10) Patent No.: US 7,943,601 B2
(45) Date of Patent: May 17, 2011

(54) 2-METHYLENE-20-METHYL-19,24,25,26,27-PENTANOR-VITAMIN D ANALOGS

(75) Inventors: Hector F. DeLuca, Deerfield, WI (US); Margaret Clagett-Dame, Deerfield, WI (US); Lori A. Plum, Arena, WI (US); Agnieszka Glebocka, Madison, WI (US); Rafal R. Sicinski, Warsaw (PL)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/343,602

(22) Filed: Dec. 24, 2008

(65) Prior Publication Data

US 2009/0170822 A1  Jul. 2, 2009

Related U.S. Application Data

(60) Provisional application No. 61/017,233, filed on Dec. 28, 2007.

(51) Int. Cl.
  *A61K 31/59* (2006.01)
  *C07C 401/00* (2006.01)
(52) U.S. Cl. .......................... 514/167; 552/653
(58) Field of Classification Search .................. 514/167; 552/653
  See application file for complete search history.

(56) References Cited

U.S. PATENT DOCUMENTS

| | | | |
|---|---|---|---|
| 4,666,634 A | 5/1987 | Miyamoto et al. | |
| 5,086,191 A | 2/1992 | DeLuca et al. | |
| 5,536,713 A | 7/1996 | Deluca et al. | |
| 5,843,928 A | 12/1998 | Deluca et al. | |
| 5,856,536 A * | 1/1999 | Deluca et al. | 552/653 |
| 5,936,133 A | 8/1999 | Deluca et al. | |
| 5,945,410 A | 8/1999 | DeLuca et al. | |
| 6,566,352 B1 | 5/2003 | DeLuca et al. | |
| 6,579,861 B2 | 6/2003 | DeLuca et al. | |
| 6,627,622 B2 * | 9/2003 | DeLuca et al. | 514/167 |
| 6,835,723 B2 * | 12/2004 | DeLuca et al. | 514/167 |

OTHER PUBLICATIONS

Arbour et al., "A Highly Sensitive Method for Large-Scale Measurements of 1,25-Dihydroxyvitamin D," Analytical Biochemistry, vol. 255, pp. 148-154, (1998).

Baggiolini et al., "Stereocontrolled Total Synthesis of 1α,25-Dihydroxycholecalciferol and 1α,25-Dihydroxyergocalciferol," Journal of Organic Chemistry, 51, pp. 3098-3108, (1986).

Collins et al, "Normal Functional Characteristics of Cultured Human Promyelocytic Leukemia Cells (HL-60) After Inducation of Differentiation by Dimethylsulfoxide," The Journal of Experimental Medicine, vol. 149, pp. 969-974, (1979).

(Continued)

*Primary Examiner* — Sabiha Qazi
(74) *Attorney, Agent, or Firm* — Andrus, Sceales, Starke & Sawall, LLP

(57) ABSTRACT

This invention discloses 2-methylene-20-methyl-19,24,25, 26,27-pentanor-vitamin D analogs, and specifically 2-methylene-20-methyl-1α-hydroxy-19,24,25,26,27-pentanor-vitamin $D_3$, and pharmaceutical uses therefore. This compound exhibits activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. This compound also has little, if any, calcemic activity and therefore may be used to treat autoimmune disorders or inflammatory diseases in humans as well as renal osteodystrophy. This compound may also be used for the treatment or prevention of obesity.

90 Claims, 5 Drawing Sheets

OTHER PUBLICATIONS

Darwish et al, "Identification of Transcription Factor That Binds to the Promoter Region of the Human Parathyroid Hormone Gene," Archives of Biochemistry and Biophysics, vol. 365, No. 1, pp. 123-130, (1999).

Fall et al, "Vitamin D Heterocyclic Analogues. Part 1: A Stereoselective Route to CD Systems with Pyrazole Rings in their Side Chains," Tetrahedron Letters 43, pp. 1433-1436, (2002).

Lythgoe et al, "Calciferol and its Relatives. Part22. A Direct Total Synthesis of Vitamin D2 and Vitamin D3," J. Chem. Soc. Perkin Trans. 1, p. 590, (1978).

Lythgoe, "Synthetic Approaches to Vitamin D and its Relatives," Chem. Soc. Rev. 9, p. 449, (1983).

Miyamoto et al, "Synthetic Studies of Vitamin D Analogues. XIV. Synthesis and Calcium Regulating Activity of Vitamin D3 Analogues Bearing a Hydroxyalkoxy Group at the 2β-Position," Chem. Pharm. Bull., vol. 41 No. 6, pp. 1111-1113, (1993).

Nishii et al, "The Development of Vitamin D3 Analogues for the Treatment of Osteoporosis," Osteoporosis Int., Suppl. 1, pp. S190-S193, (1993).

Okano et al, "Regulatory Activities of 2β-(3-Hydroxypropoxy)-1α,25-Dihydroxy-Vitamin D3, a Novel Synthetic Vitamin D3 Derivative, on Calcium Metabolism," Biochemical and Biophysical Research Communications, vol. 163 No. 3, pp. 1444-1449, (1989).

Ostrem et al, "24- and 26-homo-1,25-dihydroxyvitamin D3: Preferential activity in inducing differentiation of human leukemia cells HL-60 in vitro," Proc. Natl. Acad. Sci. USA, vol. 84, pp. 2610-2614, (1987).

Perlman et al, "1α,25-Dihydroxy-19-Nor-Vitamin D3. A Novel Vitamin D-Related Compound with Potential Therapeutic Activity," Tetrahedron Letters, vol. 31 No. 13, pp. 1823-1824, (1990).

Perlman et al, "Novel Synthesis of 19-Nor-Vitamin D Compounds," Tetrahedron Letters, vol. 32 No. 52, pp. 7663-7666, (1991).

Plum et al, "Biologically Active Noncalcemic Analogs of 1α,25-Dihydroxyvitamin D with an Abbreviated Side Chain Containing No Hydroxyl," PNAS, vol. 101 No. 18, pp. 6900-6904, (2004).

Posner et al, "Stereocontrolled Total Synthesis of Calcitriol Derivatives: 1,25-Dihydroxy-2-(4'-hydroxybutyl)vitamin D3 Analogs of an Osteoporosis Drug," Journal of Organic Chemistry, vol. 59 No. 25, pp. 7855-7861, (1994).

Posner et al, "2-Fluoroalkyl A-Ring Analogs of 1,25-Dihydroxyvitamin D3. Stereocontrolled Total Synthesis via Intramolecular and Intermolecular Diets—Alder Cycloadditions. Preliminary Biological Testing," Journal of Organic Chemistry, vol. 60 No. 14, pp. 4617-4628, (1995).

Sardina et al, "Studies on the Synthesis of Side-Chain Hydroxylated Metabolites of Vitamin D. 2. Stereocontrolled Synthesis of 25-Hydroxyvitamin D2," J. Org. Chem., 51, pp. 1264-1269, (1986).

Sicinski et al, "New 1α,25-Dihydroxy-19-Norvitamin D3 Compounds of High Biological Activity: Synthesis and Biological Evaluation of 2-Hydroxymethyl, 2-Methyl, and 2-Methylene Analogues," Journal of Medical Chemistry, 41, pp. 4662-4674, (1998).

Sicinski et al, "New Highly Calcemic 1α,25-Dihydroxy-19-Norvitamin D3 Compounds with Modified Side Chain: 26,27-Dihomo- and 26,27-Dimethylene Analogs in 20S-Series," Steroids, vol. 67, pp. 247-256, (2002).

Toh et al, "Studies on a Convergent Route to Side-Chain Analogues of Vitamin D: 25-Hydroxy-23-Oxavitamin D3," J. Org. Chem., 48, 1414, (1983).

* cited by examiner

2-METHYLENE-20-METHYL-19,24,25,26,27-PENTANOR-VITAMIN D ANALOGS

CROSS-REFERENCE TO RELATED APPLICATIONS

The present application claims the benefit of priority under 35 U.S.C. §119(e) to U.S. Provisional Application No. 61/017,233 filed on Dec. 28, 2007, the content of which is incorporated herein by reference in its entirety.

BACKGROUND OF THE INVENTION

This invention relates to vitamin D compounds, and more particularly to 2-methylene-20-methyl-19,24,25,26,27-pentanor-vitamin D analogs and their pharmaceutical uses.

The natural hormone, $1\alpha,25$-dihydroxyvitamin $D_3$ and its analog in ergosterol series, i.e. $1\alpha,25$-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., $1\alpha,25$-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, $2\beta$-hydroxy and alkoxy (e.g., ED-71) analogs of $1\alpha,25$-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of $1\alpha,25$-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of $1\alpha,25$-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In an effort to explore the 19-nor class of pharmacologically important vitamin D compounds, analogs which are characterized by the transposition of the ring A exocyclic methylene group from carbon 10 (C-10) to carbon 2 (C-2), i.e. 2-methylene-19-nor-vitamin D compounds have been recently synthesized and tested (Sicinski et al., J. Med. Chem., 41, 4662 (1998); Sicinski et al., Steroids 67, 247 (2002); DeLuca et al., U.S. Pat. Nos. 5,843,928, 5,936,133 and 6,382,071). Molecular mechanics studies, performed on these analogs, showed that a change of ring-A conformation can be expected resulting in the "flattening" of the cyclohexanediol ring. From molecular mechanics calculations and NMR studies their A-ring conformational equilibrium was established to be ca. 6:4 in favor of the conformer that has an equatorial $1\alpha$-OH. Introduction of the 2-methylene group into 19-nor-vitamin D carbon skeleton changes the character of its ($1\alpha$- and $3\beta$-) A-ring hydroxyls; they are both now in the allylic positions, similarly, as $1\alpha$-hydroxyl group (crucial for biological activity) in the molecule of the natural hormone, $1\alpha,25$-$(OH)_2D_3$. It was found that $1\alpha,25$-dihydroxy-2-methylene-19-norvitamin D analogs are characterized by significant biological potency, making such compounds excellent candidates for a variety of pharmaceutical uses.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. $1\alpha$-hydroxy-2-methylene-19-nor-pregnacalciferol is described in U.S. Pat. No. 6,566,352 while $1\alpha$-hydroxy-2-methylene-19-nor-homopregnacalciferol is described in U.S. Pat. No. 6,579,861 and $1\alpha$-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to $1\alpha,25$-dihydroxyvitamin $D_3$. Their biological activities make these compounds excellent candidates for a variety of pharmaceutical uses, as set forth in the '352, '861 and '622 patents. It is also known from Plum et al, PNAS, 101, 6900 (2004) that 2-methylene-$1\alpha$-hydroxy-19-norvitamin D analogs with truncated side chains effectively suppress parathyroid hormone levels in vivo.

SUMMARY OF THE INVENTION

The present invention is directed toward 2-methylene-20-methyl-19,24,25,26,27-pentanor-vitamin D analogs, their biological activity, and various pharmaceutical uses for these compounds. These new vitamin D compounds not known heretofore are the 19-nor-vitamin D analogs having a methylene group at the 2-position (C-2), and a 1,1-dimethylpropyl group substituted at the 17-position (C-17), i.e. the analog has a branched (1,1-dimethylpropyl)alkyl side chain containing no hydroxyl group. The preferred vitamin D analog is 2-methylene-20-methyl-$1\alpha$-hydroxy-19,24,25,26,27-pentanor-vitamin $D_3$.

Structurally these 2-methylene-20-methyl-19,24,25,26,27-pentanor-vitamin D analogs are characterized by the general formula I shown below:

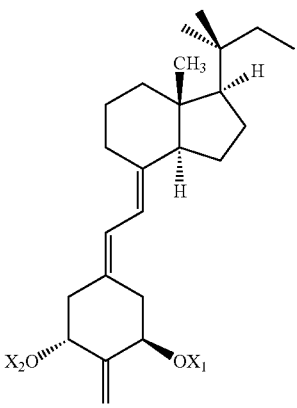

where $X_1$ and $X_2$, which may be the same or different, are each selected from hydrogen or a hydroxy-protecting group. The preferred analog is 2-methylene-20-methyl-1α-hydroxy-19,24,25,26,27-pentanor-vitamin $D_3$ which has the following formula Ia:

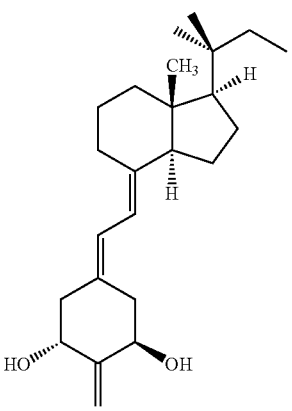

The above compounds I, particularly Ia, exhibit a desired, and highly advantageous, pattern of biological activity. These compounds are characterized by relatively high binding to vitamin D receptors, but very low intestinal calcium transport activity, as compared to that of 1α,25-dihydroxyvitamin $D_3$, and have very low ability to mobilize calcium from bone, as compared to 1α,25-dihydroxyvitamin $D_3$. Hence, these compounds can be characterized as having little, if any, calcemic activity. It is undesirable to raise serum calcium to supraphysiologic levels when suppressing the preproparathyroid hormone gene (Darwish & DeLuca, Arch. Biochem. Biophys. 365, 123-130, 1999) and parathyroid gland proliferation. These analogs having little or no calcemic activity while very active on differentiation are expected to be useful as a therapy for suppression of secondary hyperparathyroidism as well as renal osteodystrophy.

The compounds I, particularly Ia, of the invention have also been discovered to be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the invention.

The above compounds I, and particularly Ia, are also characterized by relatively high cell differentiation activity. Thus, these compounds also provide a therapeutic agent for the treatment of psoriasis, or as an anti-cancer agent, especially against leukemia, colon cancer, breast cancer, skin cancer and prostate cancer. In addition, due to their relatively high cell differentiation activity, these compounds provide a therapeutic agent for the treatment of various skin conditions including wrinkles, lack of adequate dermal hydration, i.e. dry skin, lack of adequate skin firmness, i.e. slack skin, and insufficient sebum secretion. Use of these compounds thus not only results in moisturizing of skin but also improves the barrier function of skin.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of one or more of the compounds or the pharmaceutical compositions to the subject inhibits adipocyte differentiation, inhibits gene transcription, and/or reduces body fat in the animal subject.

One or more of the compounds may be present in a composition to treat the above-noted diseases and disorders in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually or parenterally in dosages of from about 0.01 μg/day to about 1000 μg/day, preferably from about 0.1 μg/day to about 500 μg/day.

BRIEF DESCRIPTION OF THE DRAWINGS

In the drawings:

FIG. 1 is a graph illustrating the relative activity of 20DCM and 1,25(OH)$_2$D$_3$ to compete for binding with [$^3$H]-1,25-(OH)$_2$-D$_3$ to the full-length recombinant rat vitamin D receptor;

FIG. 2 is a graph illustrating the percent HL-60 cell differentiation as a function of the concentration of 20DCM and 1,25(OH)$_2$D$_3$;

FIG. 3 is a graph illustrating the in vitro transcription activity of 1,25(OH)$_2$D$_3$ as compared to 20DCM;

FIG. 4 is a bar graph illustrating the bone calcium mobilization activity of 1,25(OH)$_2$D$_3$ as compared to 20DCM; and FIG. 5 is a bar graph illustrating the intestinal calcium transport activity of 1,25(OH)$_2$D$_3$ as compared to 20DCM.

Figure 1:
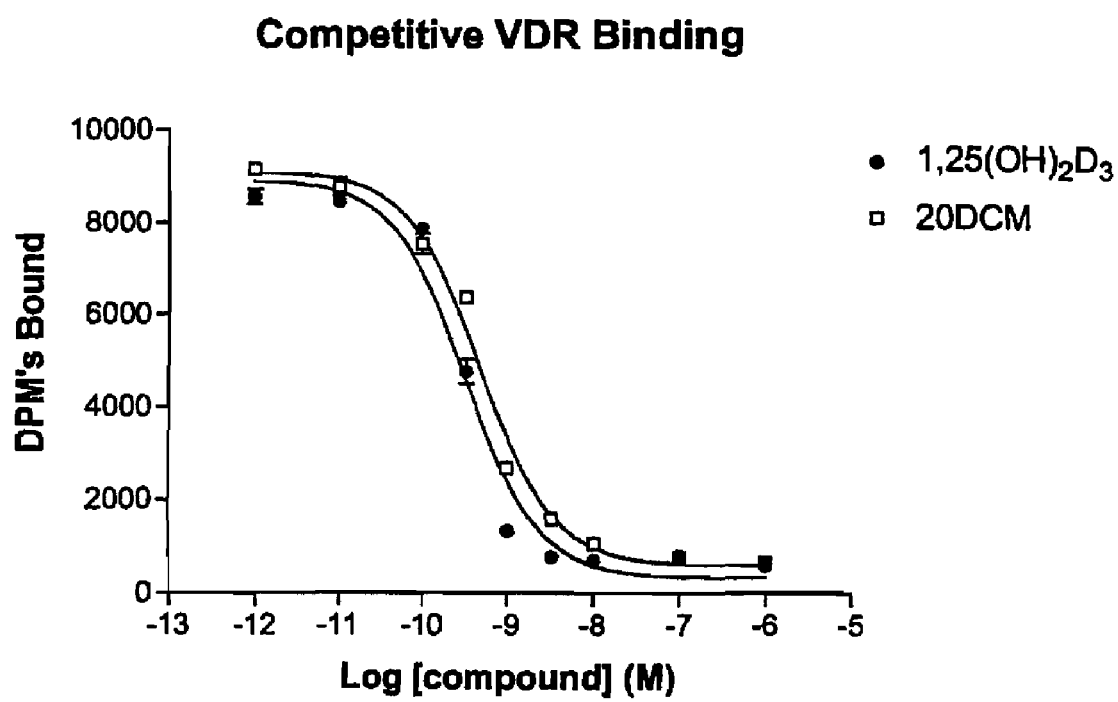
FIGS. 1-5 illustrate various biological activities of 2-methylene-20-methyl-1α-hydroxy-19,24,25,26,27-pentanor-vitamin $D_3$, hereinafter referred to as "20DCM," as compared to the native hormone 1α,25-dihydroxyvitamin $D_3$, hereinafter "1,25(OH)$_2$D$_3$."

DETAILED DESCRIPTION OF THE INVENTION 2-methylene-20-methyl-1α-hydroxy-19, 24,25,26,27-pentanor-vitamin D$_3$ (referred to herein as "20DCM") a 19-nor vitamin D analog which is characterized by the presence of a methylene substituent at the carbon 2 (C-2), and a 1,1-dimethylpropyl group substituted at the 17-position (C-17), was synthesized and tested. Such vitamin D analog seemed an interesting target because the relatively small methylene group at the C-2 position should not interfere with binding to the vitamin D receptor. Structurally, this 19-nor analog is characterized by the general formula Ia previously illustrated herein, and its pro-drug (in protected hydroxy form) is characterized by general formula I previously illustrated herein.

The preparation of 2-methylene-20-methyl-19,24,25,26,27-pentanor-vitamin D analogs having the structure I can be accomplished by a common general method, i.e. the condensation of a bicyclic Windaus-Grundmann type ketone II with the allylic phosphine oxide III to the corresponding 2-methylene-20-methyl-19,24,25,26,27-pentanor-vitamin D analog IV followed by deprotection at C-1 and C-3 in the latter compound:

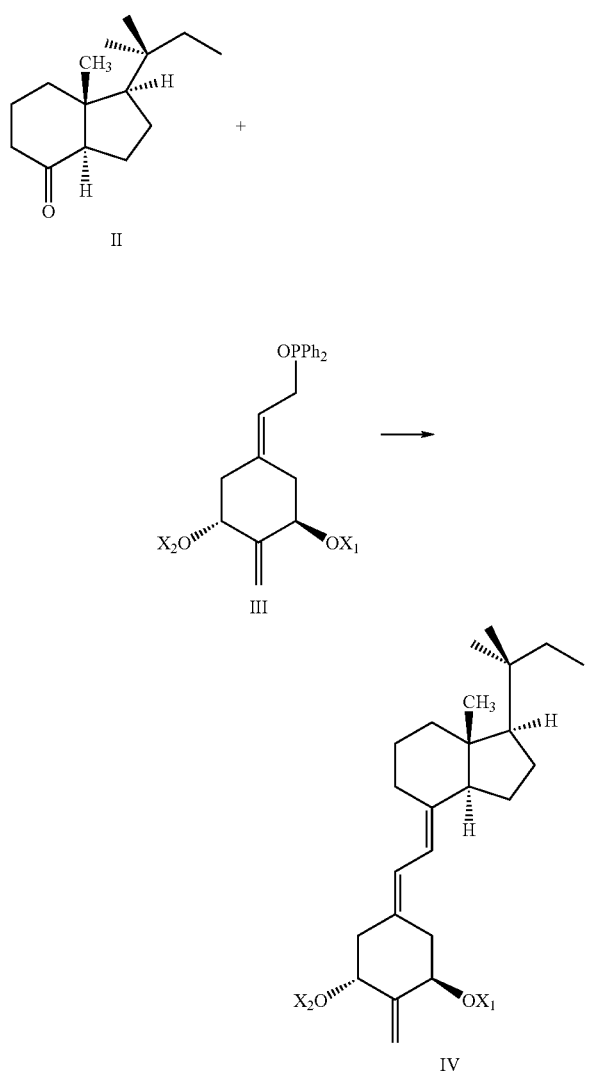

In the structures II, III and IV, groups X$_1$ and X$_2$ are hydroxy-protecting groups, preferably t-butyldimethylsilyl, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

The hydrindanone of the general structure II is not known. It can be prepared by the method shown in Scheme 1 herein (see the preparation of compound 20DCM).

For the preparation of the required hydrindanone of the structure II, new synthetic route has been developed starting from the known [Fall et al., Tetrahedron Lett., 43, 1433 (2002); Granja et al., J. Org. Chem., 58, 124 (1993)] 22-aldehyde 1. A process involving transformation of the starting benzoyloxy aldehyde 1 into the desired C,D-ring synthon 8, and its subsequent coupling with the phosphine oxide 9, is summarized by the Scheme 1. Thus, the aldehyde 1 was transformed into the mixture of isomeric E- and Z-oximes which on heating with acetic anhydride formed the expected nitrile 2. The nitrile was treated with LDA and the resulted carbanion alkylated by addition of ethyl bromide. The subsequent steps of the synthesis comprise the alkaline hydrolysis of 8β-benzoyloxy group in the obtained nitrile 3 producing the corresponding hydroxyl nitrile 4. This process is desired in view of the following chemical transformation, i.e. DIBALH reduction of the C-20 cyano group leading to the hydroxyl aldehyde 5. Direct DIBALH reduction of benzoyloxy nitrile 3 does not provide 5 in satisfactory yield whereas two-step procedure turns out to be significantly more efficient. Then, the formyl substituent at C-20 was converted into methyl group by the following two-step procedure: formation of p-tosylhydrazone 6 and its reduction with sodium cyanoborohydride. The obtained 8β-alcohol 7 was subsequently oxidized with tetrapropylammonium perruthenate to the hydrindanone 8. Wittig-Homer coupling of this Grundmann ketone with lithium phosphinoxy carbanion generated from the phosphine oxide 9 and phenyllithium gave the expected protected vitamin compound 10. This, after deprotection with tetrabutylammonium fluoride afforded 1α-hydroxy-2-methylene-20-methyl-19,24,25,26,27-pentanorvitamin D$_3$ (11). It should be noted that other 1α-hydroxy-2-methylene-19-nor-vitamin D analogs with the shortened alkyl side chains may be synthesized by the methods disclosed herein.

For the preparation of the required phosphine oxides of general structure III, a synthetic route has been developed starting from a methyl quinicate derivative which is easily obtained from commercial (b 1R,3R,4S,5R)-(−)-quinic acid as described by Perlman et al., Tetrahedron Lett. 32, 7663 (1991), DeLuca et al., U.S. Pat. No. 5,086,191, and Sicinski et al., J. Med. Chem., 41, 4662 (1998).

The overall process of the synthesis of compounds I and Ia is illustrated and described more completely in U.S. Pat. No. 5,843,928 entitled "2-Alkylidene-19-Nor-Vitamin D Compounds" the specification of which is specifically incorporated herein by reference.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

More specifically, reference should be made to the following illustrative example and description as well as to Scheme 1 herein for a detailed illustration of the preparation of compound 20DCM.

In this example specific products identified by Arabic numerals (1, 2, 3) refer to the specific structures so identified in the Scheme 1.

EXAMPLE

Chemistry. Melting points (uncorrected) were determined on a Thomas-Hoover capillary melting-point apparatus. Ultraviolet (UV) absorption spectra were recorded with a Perkin-Elmer Lambda 3B UV-VIS spectrophotometer in ethanol. $^1$H nuclear magnetic resonance (NMR) spectra were recorded at 400 and 500 MHz with a Bruker Instruments DMX-400 and DMX-500 Avance console spectrometers in deuteriochloroform. Chemical shifts ($\delta$) are reported downfield from internal Me$_4$Si ($\delta$ 0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

Preparation of 1α-hydroxy-2-methylene-20-methyl-19,24,25,26,27-pentanor-vitamin D$_3$ (11)

Referring first to SCHEME I the starting bicyclic aldehyde 1 was obtained according to the described procedure, Fall et al., Tetrahedron Lett., 43, 1433 (2002).

(a) Conversion of the Aldehyde 1 into 22-Nitrile 2

Benzoic acid(1R,3aR,4S,7aR)-1-((R)-cyano-methyl-methyl)-7a-methyl-octahydro-inden-4-yl ester (2). To a solution of a benzoyloxy aldehyde 1 (284 mg, 0.90 mmol) in anhydrous pyridine (5 mL) was added NH$_2$OH×HCl (210 mg) and the mixture was stirred at room temperature for 20 h. Then it was poured into water and extracted with ethyl acetate. The combined organic phases were separated, washed with saturated NaHCO$_3$ solution, water, and saturated CuSO$_4$ solution, dried (MgSO$_4$) and evaporated. The oily residue was purified by column chromatography on silica gel. Elution with hexane/ethyl acetate (9:1) gave pure, less polar E-oxime (167 mg) and more polar Z-oxime (105 mg, total yield 89%).

E-oxime: $^1$H NMR (400 MHz, CDCl$_3$) $\delta$ 1.09 (3H, d, J=6.7 Hz, 18-H$_3$), 1.14 (3H, s, 21-H$_3$), 2.40 (1H, m, 20-H), 5.42 (1H, narr m, 8α-H), 7.27 (1H, d, J=8.0 Hz, 22-H), 7.45 (2H, t, J~7 Hz, Ar—H), 7.56 (1H, t, J=7.4 Hz, Ar—H), 8.04 (2H, d, J=7.4 Hz, Ar—H).

Z-oxime: $^1$H NMR (400 MHz, CDCl$_3$) $\delta$ 1.09 (3H, d, J=6.7 Hz, 18-H$_3$), 1.13 (3H, s, 21-H$_3$), 3.28 (1H, m, 20-H), 5.42 (1H, narr m, 8α-H), 6.25 (1H, d, J=8.1 Hz, 22-H), 7.45 (2H, t, J7~Hz, Ar—H), 7.56 (1H, t, J=7.3 Hz, Ar—H), 8.04 (2H, d, J=7.3 Hz, Ar—H).

The solution of the oximes (both isomers, 248 mg, 0.75 mmol) in acetic anhydride (8 mL) was refluxed for 1.5 h. The reaction mixture was cooled, poured carefully on ice and extracted with toluene. Extracts were combined, washed with water, NaHCO$_3$ and brine, dried (MgSO$_4$) and evaporated. The residue was applied on a silica Sep-Pak (5 g). Elution with hexane/ethyl acetate (95:5) gave pure semicrystalline nitrile 2 (212 mg, 91%). 2: $[\alpha]^{24}_D$+81.5° (c 0.9 CHCl$_3$); $^1$H NMR (400 MHz, CDCl$_3$) $\delta$ 1.124 (3H, s, 18-H$_3$), 1.373 (3H, d, J=7.1 Hz, 21-H$_3$), 1.90 (1H, br d, J=12.8 Hz, 9β-H), 2.68 (1H, pentet, J=7.0 Hz, 20-H), 5.43 (1H, narr m, 8α-H), 7.45 (2H, t, J=7.5 Hz, Ar—H), 7.57 (1H, t, J=7.5 Hz, Ar—H), 8.03 (2H, d, J=7.4 Hz, Ar—H); HRMS (ESI) exact mass calcd for C$_{13}$H$_{20}$ON (M$^+$–C$_6$H$_5$CO) 206.1545, measured 206.1539.

(b) Alkylation of the Nitrile 2 with Ethyl Bromide

Benzoic acid-(1S,3aR,4S,7aR)-1-((S)-1-cyano-1-methyl-propyl)-7a-methyl-octahydro-inden-4-yl ester (3). n-BuLi (1.6 M in hexanes, 1.0 mL, 1.6 mmol) was added at 0° C. to the flask containing diisopropylamine (262 µL, 1.54 mmol) and THF (2 mL). The solution was stirred at 0° C. for 20 min., cooled to −78° C. and siphoned to the solution of 2 (430 mg, 1.31 mmol) in THF (1.5 mL). The resulted yellow mixture was stirred for 30 min, then HMPA (600 µL) was added and stirring was continued for another 15 min. Then CH$_3$CH$_2$Br (310 µL, 4.08 mmol) was added, and the solution was stirred at −78° C. for 40 min. Saturated NH$_4$Cl was added and the mixture was extracted with ethyl acetate. The combined organic phases were washed with water, dried (MgSO$_4$) and evaporated. The residue was applied on a silica column. Elution with hexane/ethyl acetate (95:5) resulted in pure compound 3 (280 mg, 60%; 80% based on recovered substrate). Further elution with hexane/ethyl acetate (95:5) gave unreacted 2 (107 mg). 3: $[\alpha]^{24}_D$+117.5° (c 0.2 CHCl$_3$); $^1$H NMR (400 MHz, CDCl$_3$) $\delta$ 1.023 (3H, t, J=7.4 Hz, 23-H$_3$), 1.337 (3H, s, 18-H$_3$), 1.397 (3H, s, 21-H$_3$), 2.14 (1H, br d, J=12.9 Hz, 9β-H), 5.40 (1H, narr m, 8α-H), 7.45 (2H, t, J=7.4 Hz, Ar), 7.57 (1H, t, J=7.4 Hz, Ar), 8.05 (2H, d, J=7.4 Hz, Ar).

(c) Hydrolysis of the Benzoate 3

(S)-2-((1S,3aR,4S,7aR)-4-Hydroxy-7a-methyl-octahydro-inden-1-yl)-2-methyl-butylonitrile (4). A solution of the benzoyloxy nitrile 3 (270 mg, 0.76 mmol) in 10% KOH in MeOH (12 mL) was heated at 50° C. for 18 h, poured into water and extracted with ethyl acetate. Organic phase was washed with NaHCO$_3$, water, dried (MgSO$_4$) and evaporated.

The oily residue was purified by a silica Sep-Pak (2 g). Elution with hexane/ethyl acetate (8:2) gave pure hydroxy nitrile 4 (179 mg, 99%). 4: $[\alpha]^{24}_D$+26.5° (c 0.33 CHCl$_3$); $^1$H NMR (400 MHz, CDCl$_3$) δ 1.004 (3H, t, J=7.3 Hz, 23-H$_3$), 1.349 (3H, s, 21-H$_3$), 1.240 (s, 18-H$_3$), 4.10 (1H, narr m, 8α-H).

(d) Reduction of the Nitrile 4 with DIBALH (S)-2-((1S,3aR,4S,7aR)-4-Hydroxy-7a-methyl-octahydro-inden-1-yl)-2-methyl-butyraldehyde (5). To the solution of nitrile 4 (172 mg, 0.773 mmol) in anhydrous methylene chloride (3.3 mL) a solution of DIBALH (1.5 M in methylene chloride, 1.66 mL, 2.3 mmol) was slowly added at −60° C. The solution was stirred for 1 h 30 min., then it was allowed to warm up to −30° C. during 1 h and the stirring was continued for 50 min. The mixture was carefully poured into 5% HCL and extracted with ethyl acetate. The combined organic layers were washed with NaHCO$_3$ and brine, dried (MgSO$_4$) and evaporated. The remaining residue was purified by a silica Sep-Pak (2 g). Elution with hexane/ethyl acetate (8:2) gave pure hydroxy aldehyde 5 (115 mg, 66%). 5: $[\alpha]^{24}_D$+5° (c 0.25 CHCl$_3$); $^1$H NMR (400 MHz, CDCl$_3$) δ 0.781 (3H, t, J=7.3 Hz, 23-H$_3$), 0.965 (3H, s, 21-H$_3$), 1.105 (3H, s, 18-H$_3$), 2.02 (1H, br d, J=14.2 Hz, 9β-H), 4.09 (1H, narr m, 8α-H), 9.72 (1H, s, CHO); HRMS (ESI) exact mass calcd for C$_{14}$H$_{26}$O (M$^+$+Na) 261.1831, measured 261.1847.

(e) Conversion of the Hydroxy Aldehyde 5 into a Hydrindanol 7

(1R,3aR,4S,7aR)-1-(1,1-Dimethyl-propyl)-7a-methyl-octahydro-inden-4-ol (7). A solution of the aldehyde 5 (10 mg, 0.42 μmol) and p-toluenesulfonyl hydrazide (31 mg, 0.168 mmol) in a dry methanol (0.5 mL) was stirred with molecular sieves 4 Å at 55° C. for 19 h. Then it was cooled, poured into water and extracted with toluene. The combined organic phases were washed with water, dried (MgSO$_4$), evaporated and applied on a silica Sep-Pak (2 g). Elution with hexane/ethyl acetate (85:15) gave tosylhydrazone 6 (ca. 12 mg, ca. 67%) slightly contaminated with TsNHNH$_2$. This crude tosylhydrazone was dissolved in DMF (0.15 mL) and p-TsOH (2 mg, evaporated twice with benzene) was added followed by NaBH$_3$CN (8 mg, 0.126 mmol). The mixture was stirred at 100° C. for 19 h, then it was cooled, poured into water and extracted with hexane and ethyl acetate. The combined organic phases were washed with water, dried (MgSO$_4$) and evaporated. The remaining oily residue was applied on a silica Sep-Pak (2 g). Elution with hexane/ethyl acetate (98:2) gave a hydroxy compound 7 (3 mg, 49%). 7: $[\alpha]^{24}_D$+3° (c 0.25 CHCl$_3$); $^1$H NMR (500 MHz, CDCl$_3$) δ 0.786 (3H, t, J=7.6 Hz, 23-H$_3$), 0.857 and 0.914 (3H and 3H, each s, 20-CH$_3$ and 21-H$_3$), 1.056 (3H, s, 18-H$_3$), 2.05 (1H, br d, J~10.5 Hz, 9β-H), 4.07 (1H, narr m, 8α-H).

(f) Oxidation of 7 to a Hydrindanone 8

(1R,3aR,7aR)-1-(1,1-Dimethyl-propyl)-7a-methyl-octahydro-inden-4-one (8). The solution of NMO (7.2 mg) and molecular sieves 4 Å (41 mg) in methylene chloride (0.3 mL) was stirred at room temperature for 15 min., then the solution of 7 (6 mg, 27 μmol) in methylene chloride (0.15 mL) was added followed by TPAP (0.8 mg). The resulted dark mixture was stirred for 30 min., diluted with methylene chloride and applied on a silica Sep-Pak (2 g). Elution with hexane/ethyl acetate (96:4) gave a pure ketone 8 (4.7 mg, 78%). 8: $[\alpha]^{24}_D$−43° (c 0.18 CHCl$_3$); $^1$H NMR (500 MHz, CDCl$_3$) δ 0.721 (3H, s, 18-H$_3$), 0.825 (3H, t, J=7.3 Hz, 23-H$_3$), 0.872 and 0.945 (3H and 3H, each s, 20-CH$_3$ and 21-H$_3$), 2.41 (1H, dd, J=11.0, 7.5 Hz, 14α-H).

(g) Wittig-Horner Coupling of the Ketone 8 with the Phosphine Oxide 9

1α-[(tert-Butyldimethylsilyl)oxy]-20-methyl-2-methylene-19,24,25,26,27-pentanorvitamin D$_3$ tert-Butyldimethylsilyl Ether (10). To a solution of phosphine oxide 9 (104 mg, 181 μmol) in anhydrous THF (2.0 mL) at −78° C. was slowly added phenyllithium (1.8 M in butyl ether, 101 μL, 182 μmol) under argon with stirring. The solution turned deep red. The mixture was stirred at −78° C. for 10 min and a precooled (−78° C.) solution of the ketone 8 (20 mg, 90 μmol) in anhydrous THF (0.2 mL) was slowly added. The mixture was stirred under argon at −78° C. for 1 h. Ethyl acetate and water were added, and the organic phase was washed with brine, dried (MgSO$_4$), and evaporated. The residue was dissolved in hexane, applied on a silica Sep-Pak, and eluted with hexane/ethyl acetate (99:1) to give silylated 19-norvitamin D compound 10 (39 mg, 74%). The Sep-Pak was then washed with hexane/ethyl acetate (7:3) to recover the unreacted phosphine oxide 9 (30 mg). 10: $^1$H NMR (400 MHz, CDCl$_3$) δ 0.029, 0.046, 0.068 and 0.077 (3H, 3H, 3H and 3H, each s, 4×SiCH$_3$), 0.627 (3H, s, 18-H$_3$), 0.814 (3H, t, J=7.5 Hz, 23-H$_3$), 0.867 and 0.894 (each 9H, each s, 2×Si-t-Bu), 0.864 and 0.927 (3H and 3H, each s, 20-CH$_3$ and 21-H$_3$), 2.18 (1H, dd, J=12.5, 8.5 Hz, 4β-H), 2.35 (1H, dd, J=13.5, 3.0 Hz, 10β-H), 2.46 (1H, dd, J=12.5, 4.0 Hz, 4α-H), 2.50 (1H, dd, J=13.5, 6.0 Hz, 10α-H), 2.81 (1H, dd, J~16, ~4 Hz, 9β-H), 4.42 (2H, m, 1β- and 3α-H), 4.92 and 4.97 (1H and 1H, each s, H$_2$C=), 5.82 and 6.21 (1H and 1H, each d, J=11.0 Hz, 7- and 6-H).

(h) Hydrolysis of the Silyl Protecting Groups in the 19-Norvitamin D Derivative 10

1α-Hydroxy-20-methyl-2-methylene-19,24,25,26,27-pentanorvitamin D$_3$ (11). To a solution of the protected vitamin 10 (31 mg, 53 μmol) in anhydrous THF (30 mL) was added tetrabutylammonium fluoride (1.0 M in THF, 1.4 mL, 1.4 mmol) and triethylamine (260 μL). The mixture was stirred under argon at room temperature for 18 h, poured into brine and extracted with ethyl acetate and diethyl ether. The combined organic extracts were washed with brine, dried (MgSO$_4$), and evaporated. The residue was purified by Sep-Pak (2g). Elution with hexane/ethyl acetate (7:3) gave 19-norvitamin 11 (17 mg, 89%). Compound 11 was purified further by HPLC (9.4 mm×25 cm Zorbax-Sil column, 4 mL/min) using hexane/2-propanol (9:1) solvent system. Pure 19-norvitamin 11 was collected at R$_v$ 25.2 mL. In reversed-phase HPLC (9.4 mm×25 cm Eclipse XDB-C18 column, 3 mL/min) using methanol/water (95:5) solvent system vitamin 11 was collected at R$_v$ 30 mL. 11 (20DCM): UV (in EtOH) λ$_{max}$ 245.0, 252.5, 261.5 nm; $^1$H NMR (400 MHz, CDCl$_3$) 0.637 (3H, s, 18-H$_3$), 0.814 (3H, t, J=7.0 Hz, 23-H$_3$), 0.861 and 0.924 (3H and 3H, each s, 20-CH$_3$ and 21-H$_3$), 2.30 (1H, dd, J=13.0, 8.0 Hz, 10α-H), 2.34 (1H, dd, J=13.2, 6.0 Hz, 4β-H), 2.58 (1H, dd, J=13.2, 3.8 Hz, 4α-H), 2.80 (1H, br d, J~12.5 Hz, 9β-H), 2.85 (1H, dd, J=13.0, 5.0 Hz, 10β-H), 4.48 (2H, m, 1β- and 3β-H), 5.09 and 5.11 (1H and 1H, each s, H$_2$C=), 5.87 and 6.36 (1H and 1H, each d, J=11.5 Hz, 7- and 6-H).

SCHEME 1

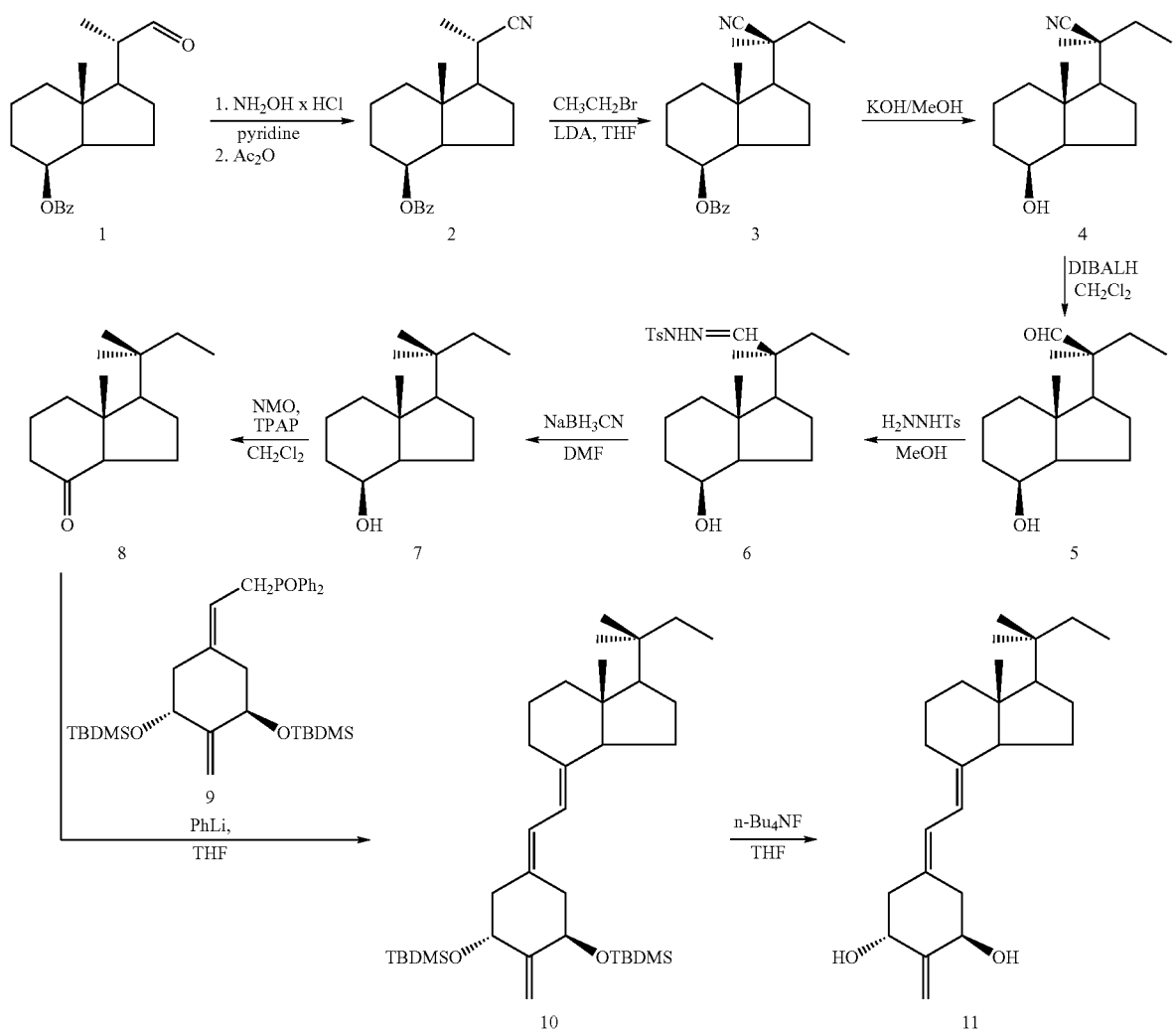

BIOLOGICAL ACTIVITY OF 2-METHYLENE-20-METHYL-1α-HYDROXY-19,24,25,26,27-PENTANOR-VITAMIN $D_3$

The introduction of a methylene group to the 2-position, and a 1,1-dimethylpropyl group substituted at the 17-position (C-17), had little effect on binding of 20DCM to the full length recombinant rat vitamin D receptor, as compared to 1α,25-dihydroxyvitamin $D_3$. The compound 20DCM bound with only slightly less affinity to the receptor as compared to the standard 1,25-$(OH)_2D_3$ (FIG. 1). 20DCM binds to the nuclear vitamin D receptor with the approximately one-half log less affinity than 1,25$(OH)_2D_3$. It might be expected from these results that compound 20DCM would have equivalent biological activity. Surprisingly, however, compound 20DCM is a highly selective analog with unique biological activity.

Figure 5:
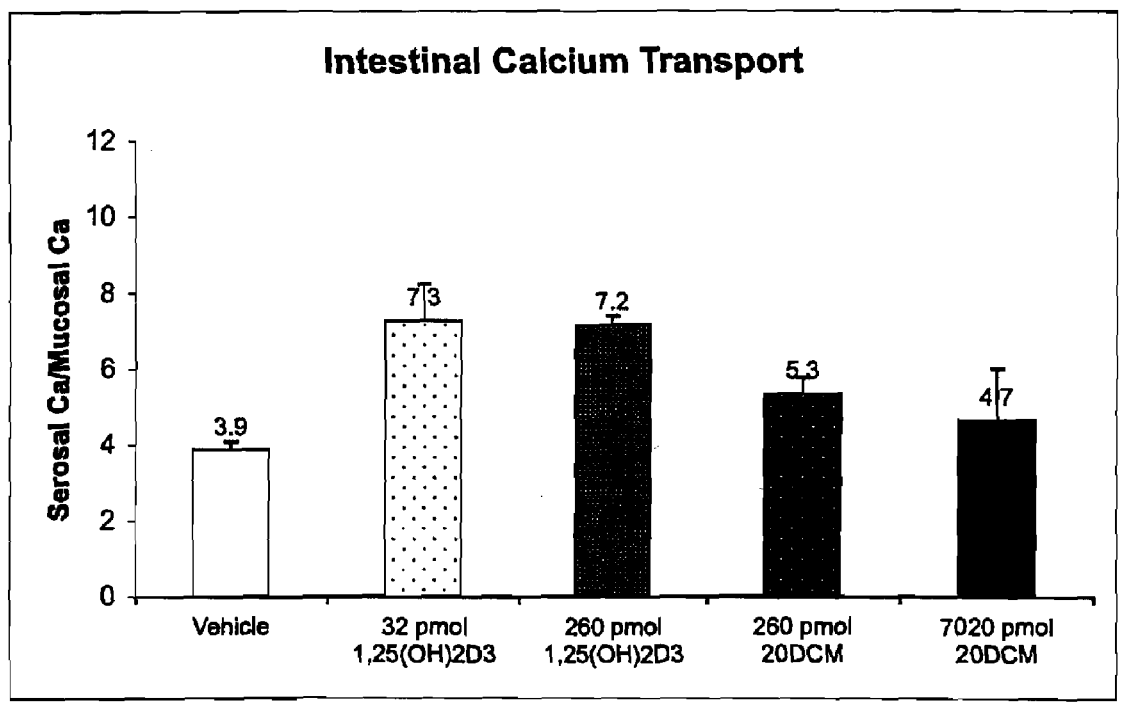

FIG. 5 shows that 20DCM has very little activity as compared to that of 1,25-dihydroxyvitamin $D_3$ (1,25$(OH)_2D_3$), the natural hormone, in stimulating intestinal calcium transport. Very little intestinal calcium transport is observed in rats administered four consecutive doses of 20DCM intraperitoneally.

Figure 4:
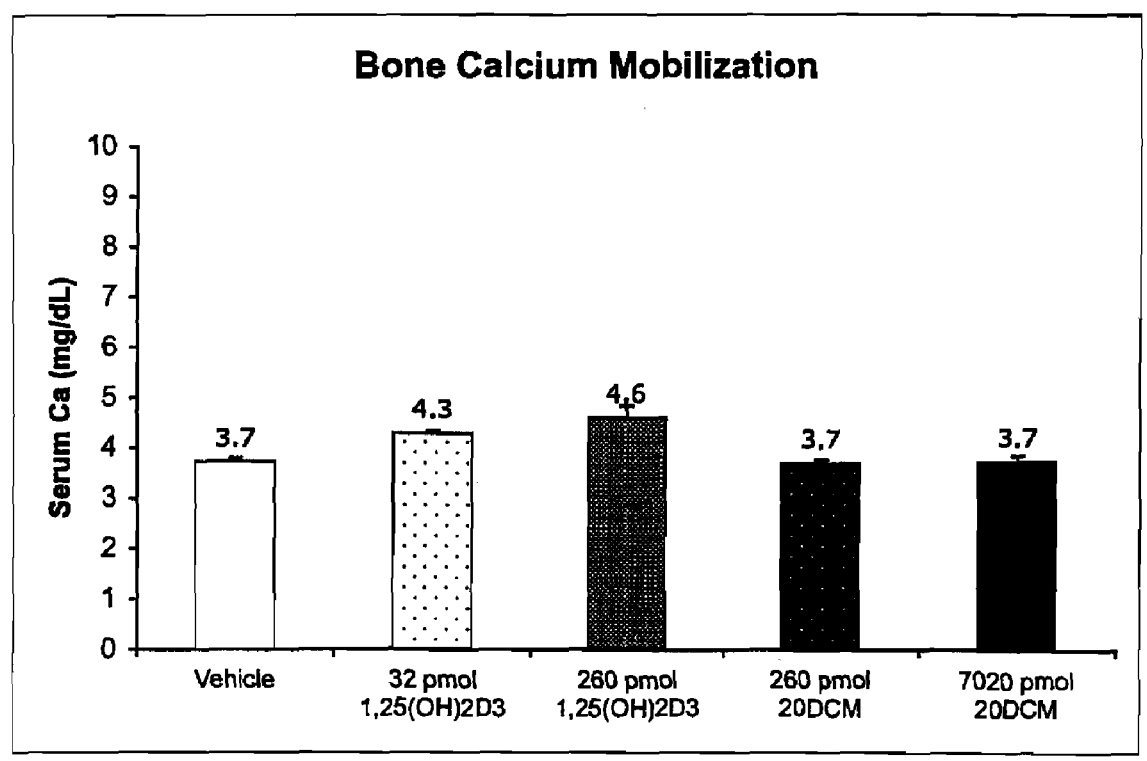

FIG. 4 demonstrates that 20DCM has very little if any bone calcium mobilization activity, as compared to 1,25$(OH)_2D_3$. 20DCM does not have any measurable activity in the bone at the dose levels tested in this batch of animals.

FIGS. 4 and 5 thus illustrate that 20DCM may be characterized as having little, if any, calcemic activity.

Figure 2:
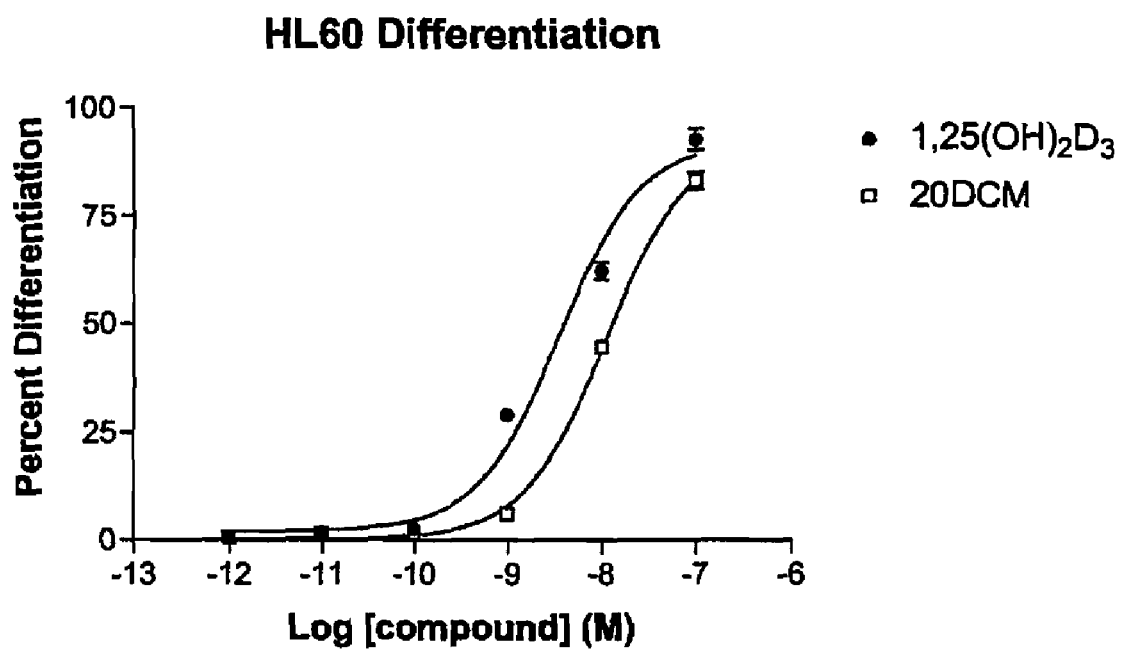

FIG. 2 illustrates that although 20DCM is about 2.5 times less potent than 1,25$(OH)_2D_3$ on HL-60 cell differentiation, it is still a good candidate for the treatment of psoriasis and cancer, especially against leukemia, colon cancer, breast cancer, skin cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 3:
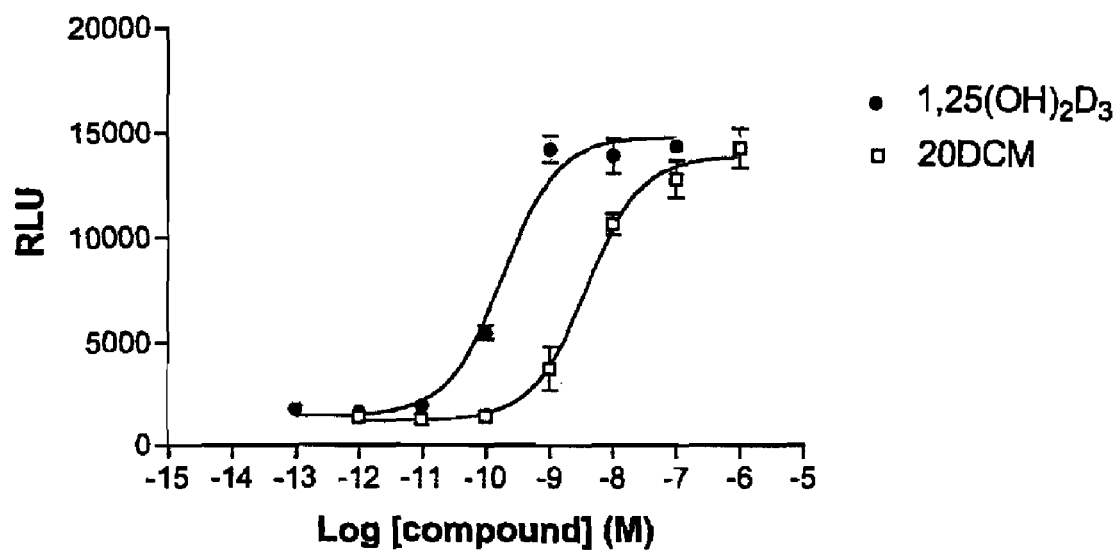

FIG. 3 illustrates that in bone cells the compound 20DCM is about 20 times less potent than 1,25$(OH)_2D_3$ in increasing transcription of the 24-hydroxylase gene. This result, together with the cell differentiation activity of FIG. 2, suggests that 20DCM will be very effective in psoriasis because it has direct cellular activity in causing cell differentiation, gene transcription, and in suppressing cell growth. These data also indicate that 20DCM may have significant activity as an anti-cancer agent, especially against leukemia, colon cancer, breast cancer, skin cancer and prostate cancer.

The strong activity of 20DCM on HL-60 differentiation suggests it will be active in suppressing growth of parathyroid glands and in the suppression of the preproparathyroid gene.

EXPERIMENTAL METHODS

Vitamin D Receptor Binding
Test Material
Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation
Test Material
Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.

RLU=relative luciferase units.

Intestinal Calcium Transport and Bone Calcium Mobilization

Male, weanling Sprague-Dawley rats were placed on Diet 11 (0.47% Ca) diet+AEK oil for one week followed by Diet 11 (0.02% Ca)+AEK oil for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

INTERPRETATION OF DATA

Summary of Biological Findings. This compound binds the VDR with slightly less affinity compared to the native hormone. While 20DCM also displays approximately 2 to 4 times less cell differentiation activity and 20 times less in vitro gene transcription activity compared to 1,25(OH)$_2$D$_3$, it remains a potentially valuable compound for therapeutic development as it possesses little, or no, activity on intestinal calcium transport and bone calcium mobilization. It could serve as a useful agent for the treatment of autoimmune diseases, cancer, secondary hyperparathyroidism, renal osteodystrophy, psoriasis or other skin conditions.

VDR binding, HL60 cell differentiation, and transcription activity. 20DCM ($K_i$=8×10$^{-11}$M) is nearly as active as the natural hormone 1α,25-dihydroxyvitamin D$_3$ ($K_i$=5×10$^{-11}$ M) in its ability to compete with [$^3$H]-1,25(OH)$_2$D$_3$ for binding to the full-length recombinant rat vitamin D receptor (FIG. 1). 20DCM is also about 2.5 times less potent (EC$_{50}$=1× 10$^{-8}$M) in its ability (efficacy or potency) to promote HL-60 cell differentiation as compared to 1α,25-dihydroxyvitamin D$_3$ (EC$_{50}$=4×10$^{-9}$M) (See FIG. 2). Also, compound 20DCM (EC$_{50}$=4×10$^{-9}$M) has about 20 times less in vivo transcriptional activity in bone cells than 1α,25-dihydroxyvitamin D$_3$ (EC$_{50}$=2×10$^{-10}$M) (See FIG. 3). These results suggest that 20DCM will be very effective in psoriasis because it has direct cellular activity in causing cell differentiation, gene transcription, and in suppressing cell growth. These data also indicate that 20DCM will have significant activity as an anti-cancer agent, especially against leukemia, colon cancer, breast cancer, skin cancer and prostate cancer, as well as against skin conditions such as dry skin (lack of dermal hydration), undue skin slackness (insufficient skin firmness), insufficient sebum secretion and wrinkles. It would also be expected to be very active in suppressing secondary hyperparathyroidism, especially in subjects having chronic kidney disease and subjects on dialysis.

Calcium mobilization from bone and intestinal calcium absorption in vitamin D-deficient animals. Using vitamin D-deficient rats on a low calcium diet (0.02%), the activities of 20DCM and $1,25(OH)_2D_3$ in intestine and bone were tested. As expected, the native hormone ($1,25(OH)_2D_3$) increased serum calcium levels at all dosages (FIG. 4). FIG. 4 shows that 20DCM has little, if any, activity in mobilizing calcium from bone. Administration of 20DCM at 260 pmol/day for 4 consecutive days did not result in mobilization of bone calcium, and increasing the amount of 20DCM to 7020 pmol/day was also without effect.

Intestinal calcium transport was evaluated in the same groups of animals using the everted gut sac method (FIG. 5). These results show that the compound 20DCM promotes intestinal calcium transport only slightly when administered at 260 pmol/day, whereas $1,25(OH)_2D_3$ promotes a significant increase at the 260 pmol/day dose. Even when 7020 pmol/day of 20DCM was administered no significant intestinal calcium transport activity was recorded, an almost 30-fold increase in dosage over the 260 pmol/day dose. Thus, it may be concluded that 20DCM is essentially devoid of intestinal calcium transport activity at these doses.

These results illustrate that 20DCM is an excellent candidate for numerous human therapies as described herein, and that it may be particularly useful in a number of circumstances such as suppression of secondary hyperparathyroidism of renal osteodystrophy, autoimmune diseases, cancer, and psoriasis. 20DCM is an excellent candidate for treating psoriasis because: (1) it has significant VDR binding, transcription activity and cellular differentiation activity; (2) it is devoid of hypercalcemic liability at relatively low doses, unlike $1,25(OH)_2D_3$; and (3) it is easily synthesized. Since 20DCM has significant binding activity to the vitamin D receptor, but has little ability to raise blood serum calcium, it may also be particularly useful for the treatment of secondary hyperparathyroidism, especially in subjects diagnosed with chronic kidney disease and subjects on dialysis, as well as the treatment of renal osteodystrophy.

These data also indicate that the compound 20DCM of the invention may be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound 20DCM of the invention.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of the compound or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly 20DCM, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 1000 µg per day of the compounds I, particularly 20DCM, preferably from about 0.1 µg to about 1000 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly 20DCM, as defined by the above formula I and Ia as the active ingredient, and a suitable carrier. An effective amount of such compound for use in accordance with this invention is from about 0.01 µg to about 1000 µg per gm of composition, preferably from about 0.1 µg to about 500 µg per gram of composition, and may be administered topically, transdermally, orally, rectally, nasally, sublingually, or parenterally in dosages of from about 0.01 µg/day to about 5000 µg/day, and preferably from about 0.1 µg/day to about 500 µg/day.

The compounds I, particularly 20DCM, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly 20DCM, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound having the formula:

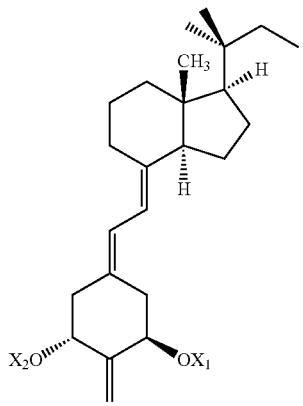

I where $X_1$ and $X_2$, which may be the same or different, are each selected from hydrogen or a hydroxy-protecting group.

2. The compound of claim 1 wherein $X_2$ is hydrogen.
3. The compound of claim 1 wherein $X_1$ is hydrogen.
4. The compound of claim 1 wherein $X_1$ and $X_2$ are both t-butyldimethylsilyl.
5. A pharmaceutical composition containing an effective amount of at least one compound as claimed in claim 1 together with a pharmaceutically acceptable excipient.
6. The pharmaceutical composition of claim 5 wherein said effective amount comprises from about 0.01 μg to about 1000 μg per gram of composition.
7. The pharmaceutical composition of claim 5 wherein said effective amount comprises from about 0.1 μg to about 1000 μg per gram of composition.
8. 2-methylene-20-methyl-1α-hydroxy-19,24,25,26,27-pentanor-vitamin $D_3$ having the formula:

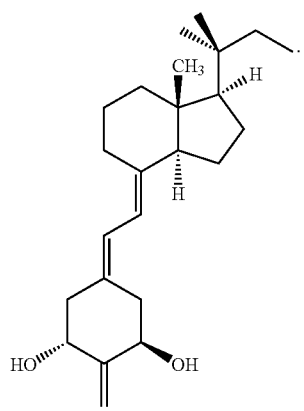

Ia

9. A pharmaceutical composition containing an effective amount of 2-methylene-20-methyl-1α-hydroxy-19,24,25,26,27-pentanor-vitamin $D_3$ together with a pharmaceutically acceptable excipient.
10. The pharmaceutical composition of claim 9 wherein said effective amount comprises from about 0.01 μg to about 1000 μg per gram of composition.
11. The pharmaceutical composition of claim 9 wherein said effective amount comprises from about 0.1 μg to about 1000 μg per gram of composition.
12. A method of treating psoriasis comprising administering to a subject with psoriasis an effective amount of a compound having the formula:

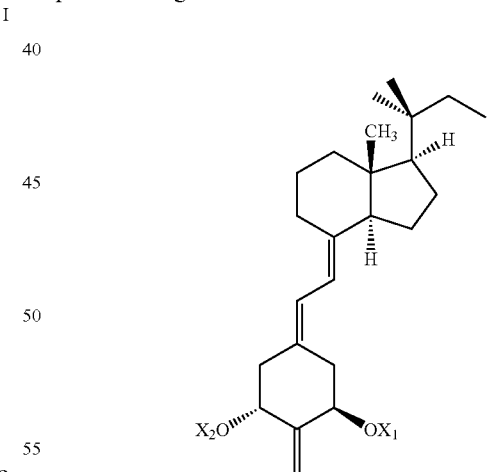

I where $X_1$ and $X_2$, which may be the same or different, are each selected from hydrogen or a hydroxy-protecting group.

13. The method of claim 12 wherein the compound is administered orally.
14. The method of claim 12 wherein the compound is administered parenterally.
15. The method of claim 12 wherein the compound is administered transdermally.
16. The method of claim 12 wherein the compound is administered topically.

17. The method of claim 12 wherein the compound is administered rectally.

18. The method of claim 12 wherein the compound is administered nasally.

19. The method of claim 12 wherein the compound is administered sublingually.

20. The method of claim 12 wherein the compound is administered in a dosage of from about 0.01 μg/day to about 1000 μg/day.

21. The method of claim 12 wherein the compound is 2-methylene-20-methyl-1α-hydroxy-19,24,25,26,27-pentanor-vitamin D$_3$ having the formula:

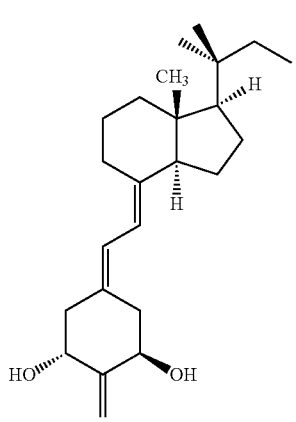

Ia

22. A method of treating a disease selected from the group consisting of leukemia, colon cancer, breast cancer, skin cancer or prostate cancer comprising administering to a subject with said disease an effective amount of a compound having the formula:

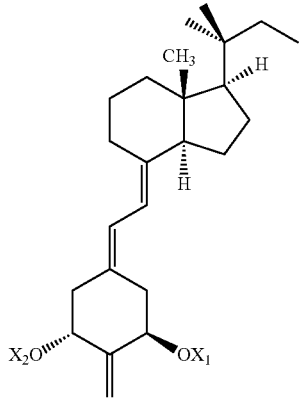

I where $X_1$ and $X_2$, which may be the same or different, are each selected from hydrogen or a hydroxy-protecting group.

23. The method of claim 22 wherein the compound is administered orally.

24. The method of claim 22 wherein the compound is administered parenterally.

25. The method of claim 22 wherein the compound is administered transdermally.

26. The method of claim 22 wherein the compound is administered rectally.

27. The method of claim 22 wherein the compound is administered nasally.

28. The method of claim 22 wherein the compound is administered sublingually.

29. The method of claim 22 wherein the compound is administered in a dosage of from about 0.01 μg/day to about 1000 μg/day.

30. The method of claim 22 wherein the compound is 2-methylene-20-methyl-1α-hydroxy-19,24,25,26,27-pentanor-vitamin D$_3$ having the formula:

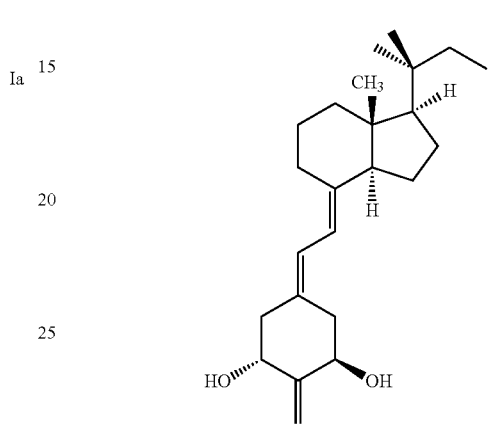

Ia

31. A method of treating an autoimmune disease selected from the group consisting of multiple sclerosis, lupus, diabetes mellitus, host versus graft rejection, and rejection of organ transplants, comprising administering to a subject with said disease an effective amount of a compound having the formula:

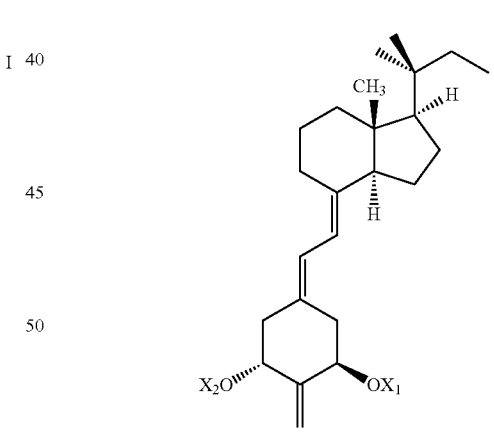

I where $X_1$ and $X_2$, which may be the same or different, are each selected from hydrogen or a hydroxy-protecting group.

32. The method of claim 31 wherein the compound is administered orally.

33. The method of claim 31 wherein the compound is administered parenterally.

34. The method of claim 31 wherein the compound is administered transdermally.

35. The method of claim 31 wherein the compound is administered rectally.

36. The method of claim 31 wherein the compound is administered nasally.

37. The method of claim 31 wherein the compound is administered sublingually.

38. The method of claim 31 wherein the compound is administered in a dosage of from about 0.01 μg/day to about 1000 μg/day.

39. The method of claim 31 wherein the compound is 2-methylene-20-methyl-1α-hydroxy-19,24,25,26,27-pentanor-vitamin D₃ having the formula:

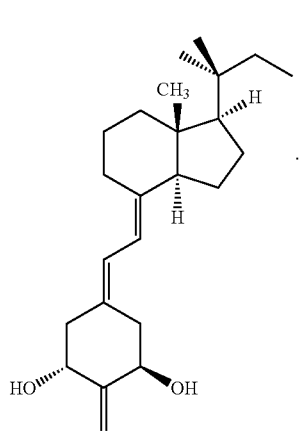

Ia

40. A method of treating an inflammatory disease selected from the group consisting of rheumatoid arthritis, asthma, and inflammatory bowel diseases, comprising administering to a subject with said disease an effective amount of a compound having the formula:

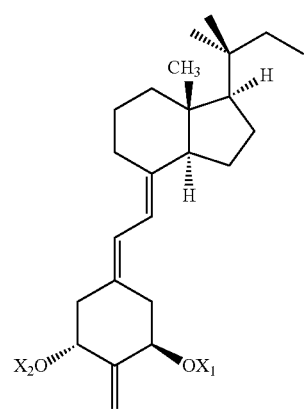

I where $X_1$ and $X_2$, which may be the same or different, are each selected from hydrogen or a hydroxy-protecting group.

41. The method of claim 40 wherein the compound is administered orally.

42. The method of claim 40 wherein the compound is administered parenterally.

43. The method of claim 40 wherein the compound is administered transdermally.

44. The method of claim 40 wherein the compound is administered rectally.

45. The method of claim 40 wherein the compound is administered nasally.

46. The method of claim 40 wherein the compound is administered sublingually.

47. The method of claim 40 wherein the compound is administered in a dosage of from about 0.01 μg/day to about 1000 μg/day.

48. The method of claim 40 wherein the compound is 2-methylene-20-methyl-1α-hydroxy-19,24,25,26,27-pentanor-vitamin D₃ having the formula:

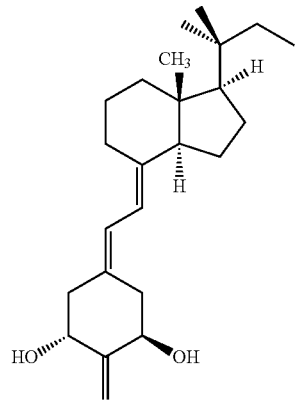

Ia

49. A method of treating a skin condition selected from the group consisting of wrinkles, lack of adequate skin firmness, lack of adequate dermal hydration and insufficient sebum secretion which comprises administering to a subject with said skin condition an effective amount of a compound having the formula:

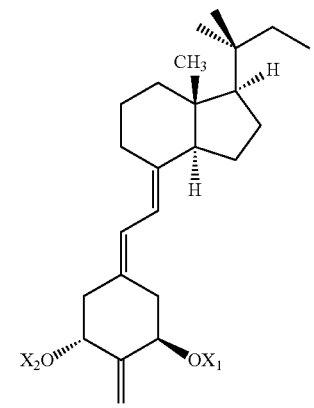

I where $X_1$ and $X_2$, which may be the same or different, are each selected from hydrogen or a hydroxy-protecting group.

50. The method of claim 49 wherein the compound is administered orally.

51. The method of claim 49 wherein the compound is administered parenterally.

52. The method of claim 49 wherein the compound is administered transdermally.

53. The method of claim 49 wherein the compound is administered topically.

54. The method of claim 49 wherein the compound is administered rectally.

55. The method of claim 49 wherein the compound is administered nasally.

56. The method of claim 49 wherein the compound is administered sublingually.

57. The method of claim 49 wherein the compound is administered in a dosage of from about 0.01 μg/day to about 1000 μg/day.

58. The method of claim 49 wherein the compound is 2-methylene-20-methyl-1α-hydroxy-19,24,25,26,27-pentanor-vitamin D₃ having the formula:

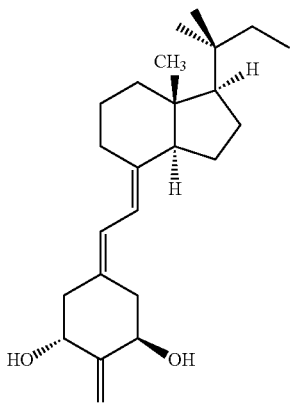

Ia

59. A method of treating renal osteodystrophy comprising administering to a subject with renal osteodystrophy an effective amount of a compound having the formula:

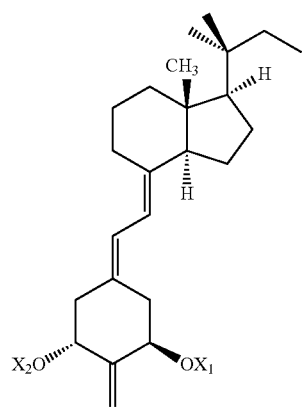

I where $X_1$ and $X_2$, which may be the same or different, are each selected from hydrogen or a hydroxy-protecting group.

60. The method of claim 59 wherein the compound is administered orally.

61. The method of claim 59 wherein the compound is administered parenterally.

62. The method of claim 59 wherein the compound is administered transdermally.

63. The method of claim 59 wherein the compound is administered rectally.

64. The method of claim 59 wherein the compound is administered nasally.

65. The method of claim 59 wherein the compound is administered sublingually.

66. The method of claim 59 wherein the compound is administered in a dosage of from about 0.01 μg/day to about 1000 μg/day.

67. The method of claim 59 wherein the compound is 2-methylene-20-methyl-1α-hydroxy-19,24,25,26,27-pentanor-vitamin D₃ having the formula:

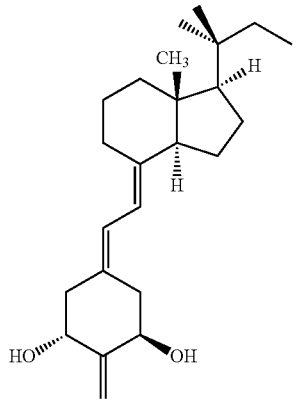

Ia

68. A method of treating obesity of an animal, inhibiting adipocyte differentiation, inhibiting SCD-1 gene transcription, and/or reducing body fat in an animal comprising administering to an animal in need thereof an effective amount of a compound having the formula

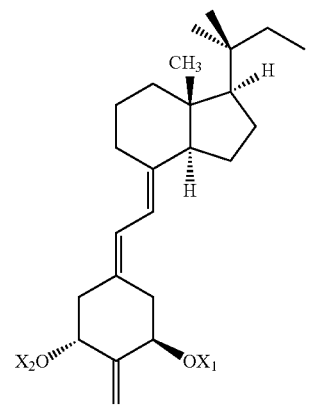

I where $X_1$ and $X_2$, which may be the same or different, are each selected from hydrogen or a hydroxy-protecting group.

69. The method of claim 68 wherein the compound is administered orally.

70. The method of claim 68 wherein the compound is administered parenterally.

71. The method of claim 68 wherein the compound is administered transdermally.

72. The method of claim 68 wherein the compound is administered rectally.

73. The method of claim 68 wherein the compound is administered nasally.

74. The method of claim 68 wherein the compound is administered sublingually.

75. The method of claim 68 wherein the compound is administered in a dosage of from about 0.01 μg/day to about 1000 μg/day.

76. The method of claim 68 wherein the compound is 2-methylene-20-methyl-1α-hydroxy-19,24,25,26,27-pentanor-vitamin haying the formula:

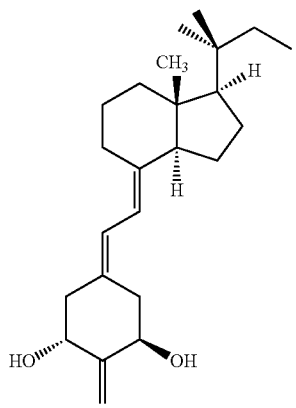

Ia

77. The method of claim 68 wherein the animal is a human.

78. The method of claim 68 wherein the animal is a domestic animal.

79. The method of claim 68 wherein the animal is an agricultural animal.

80. A method of treating secondary hyperparathyroidism comprising administering to a subject with secondary hyperparathyroidism an effective amount of a compound having the formula:

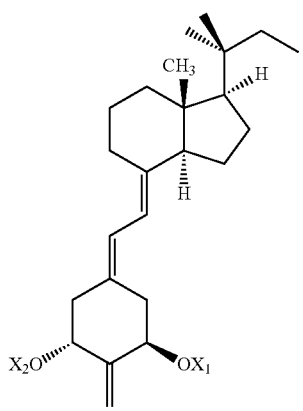

I where $X_1$ and $X_2$, which may be the same or different, are each selected from hydrogen or a hydroxy-protecting group.

81. The method of claim 80 wherein the compound is administered orally.

82. The method of claim 80 wherein the compound is administered parenterally.

83. The method of claim 80 wherein the compound is administered transdermally.

84. The method of claim 80 wherein the compound is administered rectally.

85. The method of claim 80 wherein the compound is administered nasally.

86. The method of claim 80 wherein the compound is administered sublingually.

87. The method of claim 80 wherein the compound is administered in a dosage of from about 0.01 μg/day to about 1000 μg/day.

88. The method of claim 80 wherein the compound is 2-methylene-20-methyl-1α-hydroxy-19,24,25,26,27-pentanor-vitamin $D_3$ having the formula:

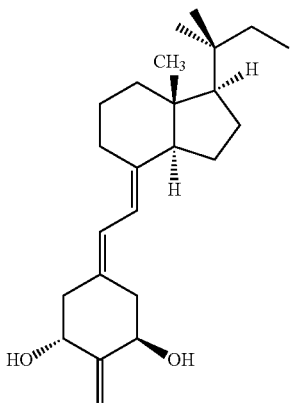

Ia

89. The method of claim 80 wherein the subject has chronic kidney disease.

90. The method of claim 80 wherein the subject is on dialysis.

* * * * *